United States Patent
Thorn et al.

(10) Patent No.: US 8,470,933 B2
(45) Date of Patent: Jun. 25, 2013

(54) COATING FOR LEAK DETECTION AND METHOD

(75) Inventors: David L. Thorn, Los Alamos, NM (US); Karl K. Jonietz, Santa Fe, NM (US); James M. Boncella, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 300 days.

(21) Appl. No.: 13/042,687

(22) Filed: Mar. 8, 2011

(65) Prior Publication Data

US 2011/0165684 A1    Jul. 7, 2011

Related U.S. Application Data

(62) Division of application No. 11/986,213, filed on Nov. 19, 2007, now Pat. No. 7,915,047.

(51) Int. Cl.
*G01N 31/10* (2006.01)
*C08F 12/08* (2006.01)

(52) U.S. Cl.
USPC ............... 525/333.3; 436/3; 442/408

(58) Field of Classification Search
USPC ............... 525/333.3; 436/3; 442/408
See application file for complete search history.

(56) References Cited

U.S. PATENT DOCUMENTS

| | | | |
|---|---|---|---|
| 2,416,061 | A | 10/1943 | McAlevy et al. |
| 4,657,700 | A | 4/1987 | Ochsner |
| 4,786,425 | A | 11/1988 | Horodysky et al. |
| 4,804,776 | A | 2/1989 | Baudin et al. |
| 4,822,743 | A | 4/1989 | Wegrzyn |
| 5,089,420 | A | 2/1992 | Albarella et al. |
| 6,121,473 | A | 9/2000 | Schrock et al. |
| 6,277,344 | B1 | 8/2001 | Hei et al. |
| 6,423,871 | B1 | 7/2002 | Jung |
| 6,476,191 | B1 | 11/2002 | Pascal et al. |
| 6,820,464 | B2 | 11/2004 | Puri et al. |
| 7,024,869 | B2 | 4/2006 | Puri et al. |
| 7,192,459 | B2 | 3/2007 | Puri et al. |
| 7,229,831 | B2 | 6/2007 | Puri |
| 7,419,635 | B2 | 9/2008 | Liu et al. |
| 2004/0031314 | A1 | 2/2004 | Flynn et al. |
| 2004/0115818 | A1* | 6/2004 | Puri et al. ................ 436/3 |
| 2004/0197919 | A1 | 10/2004 | Herman et al. |
| 2007/0246249 | A1 | 10/2007 | Kano et al. |

OTHER PUBLICATIONS

Guth, "Determination of the Configuration of Wine Lactone," Helvetica Chimica Acta, Sep. 1996, pp. 1559-1571, vol. 79, No. 6.
International Search Report and Written Opinion issued on Dec. 24, 2008 for International Application No. PCT/US08/12546 filed on Nov. 7, 2008 (8 pages).

* cited by examiner

*Primary Examiner* — Ling Choi
*Assistant Examiner* — Chun-Cheng Wang
(74) *Attorney, Agent, or Firm* — Samuel L. Borkowsky

(57) ABSTRACT

A coating is used to detect a fluid leak.

12 Claims, No Drawings

COATING FOR LEAK DETECTION AND METHOD

RELATED APPLICATIONS

This application is a divisional of U.S. patent application Ser. No. 11/986,213 filed Nov. 19, 2007, hereby incorporated by reference.

STATEMENT REGARDING FEDERAL RIGHTS

This invention was made with government support under Contract No. DE-AC52-06NA25396 awarded by the U.S. Department of Energy awarded by the U.S. Department of Energy. The government has certain rights in the invention.

FIELD OF THE INVENTION

The present invention relates generally to leak detection and more particularly to chemical coatings that may be used for detecting and locating fluid leaks.

BACKGROUND OF THE INVENTION

In the emerging "hydrogen economy," it is anticipated that hydrogen gas will be a very widely used fuel, perhaps the fuel of choice for millions of fuel cells that could be used in vehicles, portable electronic devices, and small motorized devices (lawn mowers, snow blowers, and the like). However, there remain safety concerns about using hydrogen as fuel for these purposes. Hydrogen gas can leak through the tiniest imperfections in tanks, lines, or joints. Accumulated hydrogen is extremely flammable and, because it is odorless and colorless, hydrogen gas gives no warning of its presence.

There has been considerable interest in developing chemical compounds that can be added to hydrogen that provide an easily detectable and recognizable odor so that anyone with a normal sense of smell could tell immediately if there were a hydrogen leak in the vicinity and take corrective action before an explosion or fire occurred. This approach has been used for many years to make natural gas and household gas immediately recognizable in the event of a gas leak or if a gas appliance (a gas furnace, gas stove, and the like) is releasing the gas, which has greatly contributed to the safe use and widespread acceptance of gas in households.

There are problems associated with adding odorants to hydrogen. Many odorizing compounds contain sulfur or nitrogen. These odorants cannot be used with devices such as fuel cells. Typical fuel cells have a platinum anode, and these types of odorants can "poison" the platinum anode or the electrolyte membrane and degrade the fuel cell's performance, even if present in very small amounts. For fuel cells that operate at lower temperatures, an odorant will not ordinarily be destroyed as it passes through the fuel cell into the exhaust, so some additional means must be taken to remove the odorant and prevent the normal exhaust from being mistaken for a hydrogen leak. In addition, hydrogen is so buoyant in air that leaking hydrogen and most of any odorant added to the hydrogen will float to accumulate in headspace. If this happens, there is risk that dangerous amounts of hydrogen will accumulate in the headspace before the odor of odorant additives can be noticed.

There are other fluids besides hydrogen that do not possess a distinctive odor or color and that are therefore difficult for people to detect directly, where the intended use of the substance does not easily admit adding an odorizing compound, and where a leak could be harmful or dangerous. One such substance is methanol. Methanol is used in direct-methanol fuel cells and other devices. Methanol is toxic, and ingesting sub-lethal doses has caused blindness, so consumers generally are concerned about exposure to methanol.

A material that could be applied to a surface of the container, to the container housing, to pipes, fittings, or other connections to the container, or to surfaces near the container as a coating that would respond to fluids such as hydrogen and/or methanol by chemically reacting with the fluid to produce a color change or release an detectable odorant could alert people to a leak yet not require anything being added directly to the fluid itself.

SUMMARY OF THE INVENTION

In accordance with the purposes of the present invention, as embodied and broadly described herein, an aspect of the present invention includes a method for detecting a fluid leak. The method involves applying to a surface a coating comprising a polymer that undergoes a chemical reaction with a fluid to produce a volatile odorant; allowing the coating to become exposed to fluid that chemically reacts with the polymer to generate the volatile odorant; and detecting the odorant.

Another aspect of the invention involves a coating that includes a polymer that chemically reacts with fluid to generate an odorant.

DETAILED DESCRIPTION

The present invention relates to leak detection and coatings used for detecting fluid leaks. An aspect of the invention involves applying a coating on an exterior surface so that fluid from a leak can react with the coating to produce an odorant and/or a color change. The coating could be applied on an exterior surface of a container that stores the fluid. The coating could also be applied on fluid storage or transfer lines, room walls, floors, ceilings, valves, fittings, and on other surfaces such as the surface of a fuel cell. The coating would ordinarily go unnoticed. Leaked gas or liquid undergo a chemical reaction with the coating. For example, if the coating was applied to a fluid container and there were a leak of a fluid such as hydrogen or methanol from the container, then an odorant would be released from the point of leakage. Depending on the coating, a change in appearance, such as a color change, could also be observable at the leaking point.

Some odorants useful with the invention have a strong and easily recognizable odor. The coating may also undergo a change in appearance when exposed to small amounts of a confined fluid.

An aspect of this invention involves detecting and easily locating a hydrogen gas leak. Detecting such a leak would greatly reduce consumers' fears about the safety of using hydrogen as a fuel and could significantly reduce the risk of serious accidents. A coating that could respond to methanol could alert consumers to small leaks of methanol and improve consumer confidence in using methanol for powering direct-methanol fuel cells in devices such as cellular telephones and laptop computers.

Coatings used with this invention are typically non-odorous when they are isolated from the fluid. However, when they come into contact with hydrogen, methanol, or other fluids, they react with the fluid and release the odorants that alert people in the vicinity of the leak and allow the people to respond before dangerous levels of the substance were released.

SCHEME 1 below illustrates the preparation of an embodiment polymer by reacting commercially available MERRI-FIELD RESIN (having polymer backbone (P) attached to chlorobenzyl groups) with a compound that is a precursor to the odorant "wine lactone". Wine lactone has a recognizable odor at a concentration of $10^{-14}$ gram per liter of air (see: Guth. Helv. Chim. Acta (1996) vol. 79, pp. 1559-1571, incorporated by reference). SCHEME 1 also shows a chemical reaction that occurs when a coating including the polymer and a catalyst is exposed to a fluid leak of hydrogen gas (H$_2$). amine. The embodiment shown illustrates the release of odorant putrescine upon reaction with hydrogen.

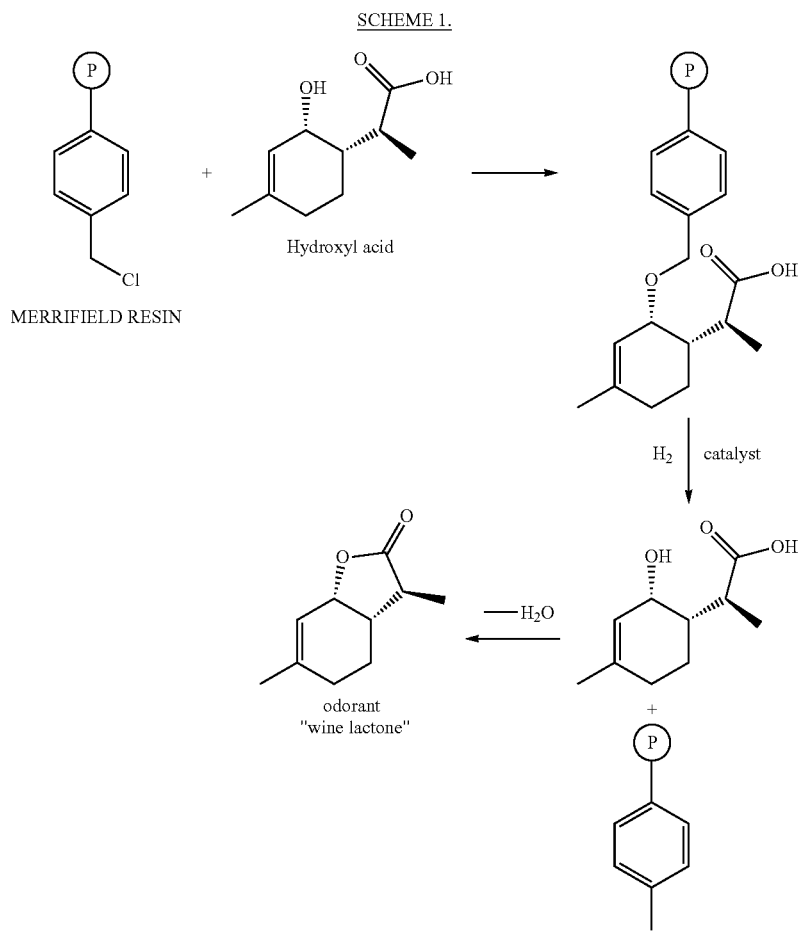

As SCHEME 1 shows, MERRIFIELD RESIN reacts with precursor hydroxyl-acid compound to form the embodiment polymer, which includes benzyl ether groups. The embodiment polymer is mixed with a catalyst such as palladium or a compound having palladium. This mixture is applied to a surface as a coating. When the coating is exposed to hydrogen from a leak, the polymer coating undergoes a hydrogenolysis reaction resulting in cleavage of a benzyl-oxygen bond and the release of the hydroxyl-acid, which is the odorant precursor that subsequently releases a molecule of water and is converted into the odorant.

Hydrogenolytic liberation of odorants from polymeric benzyl ethers, such as the one shown in SCHEME 1, is both general and flexible and it should be understood that the invention is not limited to the use of the specific precursor alcohol and odorant shown in SCHEME 1. Many other odorant compounds can react with MERRIFIELD RESIN to produce a polymer that can undergo hydrogenolysis with hydrogen from a fluid leak to release odorant precursor, or odorant. Hydroxylfuranones such as 5-ethyl-3-hydroxy-4-methyl-2 (5H)-furanone (i.e. "maple lactone"), for example, react with MERRIFIELD RESIN to form embodiment polymers that release odorant hydroxylfuranones that are easily recognized and detected at concentrations below 1 part per billion (ppb) in air.

SCHEME 2 illustrates another embodiment of the invention. In this embodiment, a polymer releases an odorant

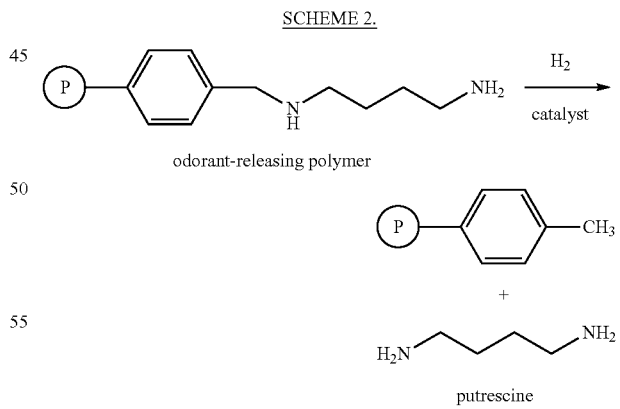

The chemical reaction of MERRIFIELD RESIN with 1,4-diaminobutane or 1,5-diaminopentane (i.e. putrescine or cadaverine, respectively) produces an embodiment odorant-releasing polymer. The odorant-releasing polymer is mixed with a catalyst (a finely divided catalyst having at least some palladium, for example). The mixture is applied to a surface as a coating. When the coating is exposed to hydrogen, a chemical reaction occurs resulting in a hydrogenolysis reaction and the release of putrescine or cadaverine from the polymer.

SCHEME 3 illustrates another embodiment that is illustrative of the generation of odorants from polymers.

SCHEME 3.

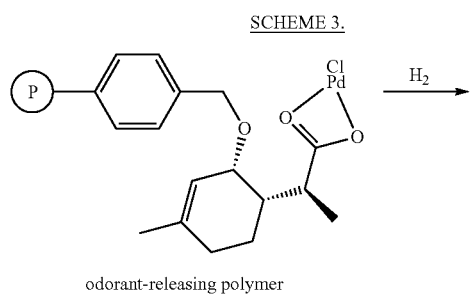

odorant-releasing polymer attack on the chloromethyl group of the resin. This polymer is mixed with a pH indicator, and the mixture is coated on a surface. When the coating is exposed to $H_2$, the Pd(II) carboxylate reacts with the $H_2$. The result is a reduction in oxidation state from Pd(II) to Pd(0) and the formation of acid. The acid reacts with the pH indicator to produce a color change. The Pd(0) that forms acts as a catalyst for subsequent hydrogenolysis of the benzylic ether to liberate hydroxy-acid, which loses a water molecule to form the "wine lactone". SCHEME 3 illustrates the following aspects of the invention: (i) using hydrogenolysis to liberate an odorant, (ii) using hydrogen to reduce Pd(II) to Pd(0) which becomes a catalyst for subsequent hydrogenolysis, (iii) using hydrogen to reduce Pd(II) as a means for locating a fluid leak, (iv) using hydrogen-produced Pd(0) as a catalyst to hydrogenolytically liberate an odorant, and (v) using the odorant for leak detection.

SCHEME 4 illustrates another embodiment concerned with producing odorants from polymers.

SCHEME 4

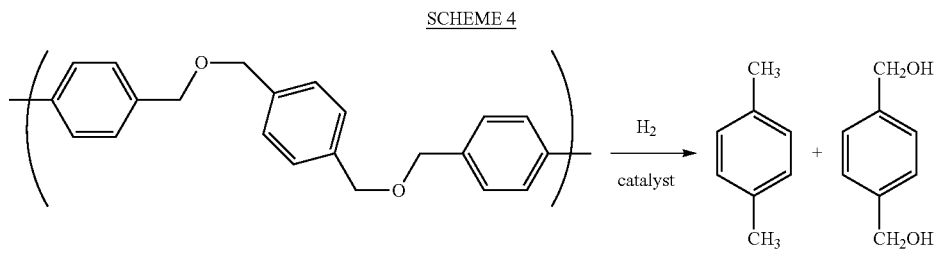

-continued

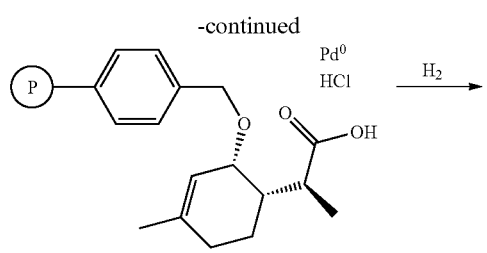

A polymer based on 1,4-benzenedimethanol, as illustrated in SCHEME 4, is mixed with a catalyst (such as palladium or a palladium compound). A membrane or coating of the mixture could be used as an indicator of a hydrogen leak. The membrane or coating would be weakened or ruptured by the presence of hydrogen. An odorant could be encapsulated within such a membrane. When the membrane ruptures, the odorant would be released.

SCHEME 5 shows an embodiment illustrating the use of hydrogen to activate a catalyst that ruptures a polymer and releases an odorant.

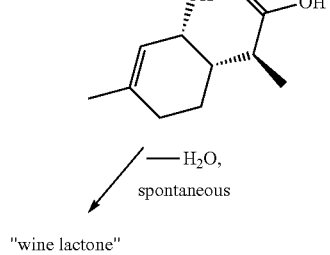

"wine lactone"

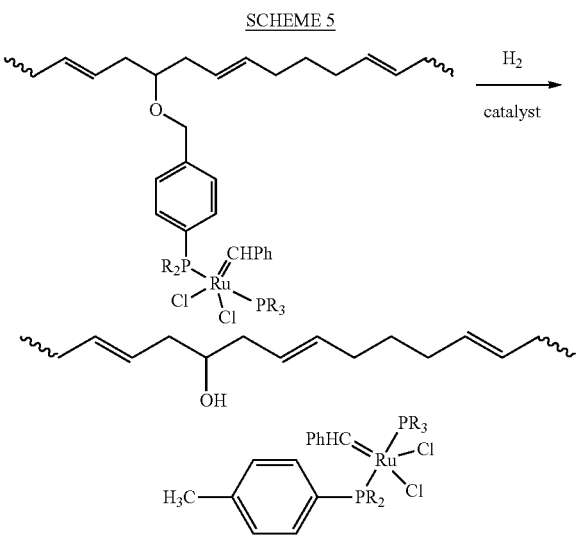

SCHEME 3 shows an embodiment odorant-releasing polymer having a MERRIFIELD RESIN backbone, a benzylic ether group, and a palladium(II) carboxylate group. The synthesis of the odorant-releasing Pd-containing polymer is accomplished using standard techniques for the synthesis of Pd carboxylate complexes. Immobilization of this precursor on Merrifield resin is accomplished by deprotonation of the hydroxide group of the wine lactone precursor and addition is of the resultant anion to the Merrifield resin via nucleophilic

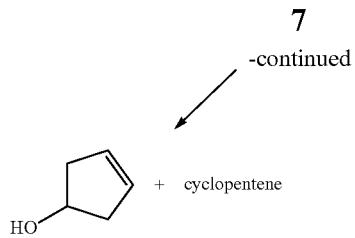 + cyclopentene

In SCHEME 5, hydrogenolysis of a polymer detaches an olefin metathesis catalyst. SCHEME 5 offers an amplification effect by allowing very small amounts of hydrogen to release relatively large amounts of odorant. The R group is independently selected from aryl and alkyl having from 1-20 carbons (for example: phenyl, methylphenyl, ethylphenyl, methyl, ethyl, propyl, isopropyl, butyl, isobutyl, pentyl, hexyl, etc.). The polymer shown can be in the form a polymer membrane, and rupturing the polymer membrane would result in release of odorant. SCHEME 5 illustrates a ruthenium (Ru) based metathesis catalyst in a side chain. Thus, the catalyst is covalently attached to the polymer backbone via a benzylic-ether linkage. The benzylic-ether linkage distances the metal center from the polymer backbone and prevents a chemical reaction between the metal is center and polymer backbone. The polymer backbone includes olefins that can react with metal center. As SCHEME 5 shows, the polymer reacts with hydrogen first to detach the side chain, which frees the catalyst from the polymeric backbone. The now free catalyst can begin a metathesis reaction with the polymer that forms molecules of cyclopentene and cyclopentenol from the polymer backbone. These small molecules are odorants. Some aspects of the invention illustrated by SCHEME 5 include (i) inactivation of a metathesis catalyst awaiting release when a specific substance (hydrogen, for example) is exposed to the polymer; (ii) a polymer and method wherein release of a metathesis catalyst from the polymer indicates detection of a specific substance (such as hydrogen); and (iii) using a metathesis catalyst to depolymerize a polymer to generate an odorant.

In another aspect of the invention, a method for detecting a hydrogen gas leak involves preparing a mixture of an acid-sensitive pH indicator and a lightly colored salt (or salts) of Pd(II). When the mixture is coated on a surface and the coating is exposed to hydrogen gas, Pd(II) is reduced to Pd(0) and acid is produced that reacts with the pH indicator to produce a color change. Representative Pd(II) salts include palladium chloride, palladium bromide, palladium iodide, and palladium sulfate. A representative pH indicator is methyl red (2-[4-(dimethylamino)phenylazo]benzoic acid), which is yellow at a pH of about 6 and higher but becomes pink-red when it reacts with acid. Other pH indicators could also be used for this purpose.

In yet another aspect of the invention, another method for detecting a hydrogen gas leak involves preparing a mixture of an oxidizing agent and a salt (or salts) of Pd(II). When the mixture is coated on a surface and the coating is exposed to hydrogen gas, Pd(II) is reduced to Pd(0), which reacts with the oxidizing agent to produce a color change. Representative Pd(II) salts include palladium chloride, palladium bromide, palladium iodide, and palladium sulfate. A representative oxidizing agent is phosphomolybdic acid, which is ordinarily colorless or pale in color and becomes green, greenish-blue or blue when it reacts with a reducing agent. Another representative oxidizing agent is the redox indicator tris(phenanthroline)iron(III), which is blue in color in the iron(III) oxidation state but becomes red when reduced. Other redox indicators could be employed for this purpose.

The coating and method can be used with hydrogen-powered vehicles and with smaller hydrogen-powered motorized units (e.g. lawn mowers, snow blowers), as a coating on hydrogen storage tanks and storage lines which would alert the operator if there were a hydrogen leak. The invention can also be used by forming a coating on surfaces of, for example, the ceiling or walls of a enclosure (a garage, for example) so that if a hydrogen-powered vehicle or motorized unit leaked hydrogen while in the garage the coating would release odorant and/or be noticeably discolored. The owner would detect the odorant or color change. Detection would alert the owner to a probable hazard before starting the vehicle or motorized unit. The coating and method could also be used to coat the power-cell chamber of a portable electronic device, again to alert the operator if methanol or hydrogen were leaking from the device. The coating and method would be useful in applications where methanol, hydrogen or other substances are produced and stored where it would be valuable to have the odor and visual indication of a leak.

The coating and method can be used to detect fluid leaks from a fuel cell. Some advantages of the invention with regard to detection of a fuel leak from a fuel cell, compared to known leak detection methods involving odorants include the following: (i) the odorant is not present in the fluid itself, (ii) there are no issues with "poisoning" the components of a fuel cell from odorants present in the fluid, (iii) the natural exhaust of the fuel cell will be non-odorous.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for detecting a fluid leak comprising:
   applying to a surface a coating comprising a polymer and a catalyst that catalyzes a reaction with the polymer and fluid from the fluid leak to produce an odorant;
   allowing the coating to become exposed to the fluid; and
   detecting the odorant.

2. The method of claim 1, wherein the polymer and catalyst are chemically bonded to each other before allowing the coating to become exposed to the fluid.

3. The method of claim 1, wherein the fluid comprises hydrogen gas or methanol.

4. The method of claim 1, wherein the catalyst comprises palladium or a compound having palladium.

5. The method of claim 1, wherein the polymer comprises a polymer backbone and a side chain attached to the polymer backbone, wherein at least part of the side chain detaches from the polymer and the odorant forms from the detached portion of the side chain.

6. The method of claim 5, wherein the polymer is of the formula

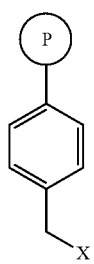

wherein P is a polymer backbone and X is chosen from an isobutyrate group or a group of the formula

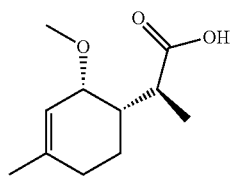

or —NH(CH$_2$)$_4$NH$_2$ or —NH(CH$_2$)$_5$NH$_2$.

7. The method of claim 1, wherein the polymer backbone P comprises a polymer backbone and a side chain attached to the polymer backbone, wherein the odorant forms from the polymer backbone.

8. The method of claim 7, wherein the polymer backbone comprises olefins, wherein the side chain reacts with fluid and thereafter detaches from the polymer and forms a catalyst that reacts with polymer backbone and fluid to depolymerize the polymer backbone and form odorant molecules or odorant molecule precursors from the polymer backbone.

9. The method of claim 8, wherein the polymer is of the formula

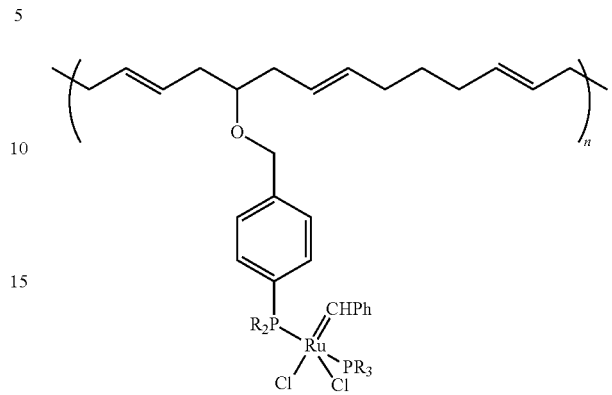

wherein n is an integer greater than 1 and R is selected independently from aryl and alkyl having 1 to 20 carbons.

10. The method of claim 1, wherein said coating further comprises a chemical that produces a detectable color change as a result of an acid-base reaction after the coating is exposed to the fluid.

11. The method of claim 10, wherein the chemical that produces a detectable color change comprises an acid-base indicator.

12. The method of claim 1, wherein said coating further comprises a chemical that produces a detectable color change as a result of a redox reaction after the coating is exposed to the fluid.

* * * * *